United States Patent [19]

Crutchfield et al.

[11] 4,158,635
[45] Jun. 19, 1979

[54] DETERGENT FORMULATIONS CONTAINING TETRAHYDROPYRAN OR 1,4-DIOXANE POLYCARBOXYLATES AND METHOD FOR USING SAME

[75] Inventors: Marvin M. Crutchfield, Creve Coeur; Charles J. Upton, Ballwin, both of Mo.

[73] Assignee: Monsanto Company, St. Louis, Mo.

[21] Appl. No.: 950,182

[22] Filed: Oct. 10, 1978

Related U.S. Application Data

[63] Continuation of Ser. No. 857,070, Dec. 5, 1977, abandoned.

[51] Int. Cl.$^2$ ............ C11D 3/20; C11D 3/08; C11D 7/54
[52] U.S. Cl. .............. 252/99; 252/89 R; 252/135; 252/527; 252/546; 252/DIG. 11; 260/340.6
[58] Field of Search ........... 252/89, 99, 135, 532, 252/535, 539, DIG. 11, 551, 554, 555, 558; 260/345.7, 345.8, 340.6

[56] References Cited

U.S. PATENT DOCUMENTS

| 3,817,863 | 6/1974 | Shen | 252/89 |
| 3,835,163 | 9/1974 | Rapko | 260/347.3 |
| 3,923,841 | 12/1975 | Crutchfield | 260/347.3 |
| 4,071,476 | 1/1978 | Patterson | 252/557 |

*Primary Examiner*—P. E. Willis, Jr.
*Attorney, Agent, or Firm*—S. M. Tarter; E. P. Grattan; F. D. Shearin

[57] ABSTRACT

This disclosure concerns:
(a) compounds having the molecular structure represented by the formula

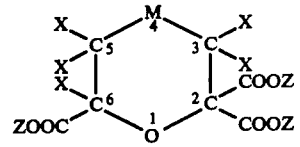

wherein M is O or $CY_2$, where Y is H or lower alkyl ($C_1$ to $C_4$), X is selected from the group consisting of H, lower alkyl ($C_1$ to $C_4$), or COOZ, Z represents H, R or a salt forming ion from the group alkali metal, ammonium, or trialkanolammonium, and R is an alkyl group (branched or straight chain) having up to about $C_{20}$ in the chain
(b) a process for producing the compounds of (a) by the basic carboxylation of compounds represented by the formula

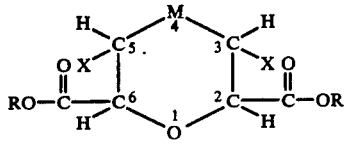

wherein M, X and R are as described in (a),
(c) solid and liquid detergent compositions comprising compounds of (a) and
(d) washing processes employing the compounds of (a) and/or the compositions of (c).

10 Claims, No Drawings

DETERGENT FORMULATIONS CONTAINING TETRAHYDROPYRAN OR 1,4-DIOXANE POLYCARBOXYLATES AND METHOD FOR USING SAME

This is a continuation of application Ser. No. 857,070, filed Dec. 5, 1977 now abandoned.

BACKGROUND OF THE INVENTION

The invention relates to tetrahydropyran and 1,4-dioxane polycarboxylate compounds, methods for preparing such compounds, liquid and solid detergent compositions comprising them, the use of the compounds as detergent builders, calcium and magnesium sequestrants, scale dissolvers and the like and the use in washing processes of the compounds and detergent compositions containing such compounds.

The compounds have utility in complexing various metal ions, such as, calcium and magnesium ions which contribute to hardness in water. In combination with detergent compounds and compositions, the compounds are useful in improving the cleaning ability of the detergent. Thus, the primary areas of utility for the compounds are in water treatment, e.g., for water softening and as detergency builders and threshold agents.

DESCRIPTION OF THE PRIOR ART

U.S. Pat. No. 3,835,163, issued Sept. 10, 1974, to John N. Rapko, discloses tetrahydrofuran polycarboxylic acids, esters and salts and their use as complexing agents and detergency builders.

U.S. Pat. No. 3,923,841, issued on Dec. 2, 1975 to Marvin M. Crutchfield, discloses a method of making tetrasodium or potassium tetrahydrofuran-2,2,5,5-tetracarboxylates and hydrates thereof and U.S. Pat. No. 3,817,863, issued June 18, 1974, to Chung Yu Shen discloses detergent formulations comprising such compounds as builders.

All of the foregoing patents are assigned to Monsanto Company, as is the present application.

The compounds, compositions and processes of this invention are structurally and functionally different from the disclosures of the prior art.

SUMMARY OF THE INVENTION

The invention relates to tetrahydropyran and 1,4-dioxane polycarboxylates, methods for making such compounds, compositions containing such compounds, and methods for employing such compounds and compositions.

The compounds of the invention have the molecular structure represented by the following general formula:

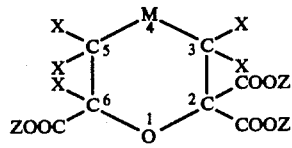

wherein M is O or $CY_2$, where Y is H or lower alkyl ($C_1$ to $C_4$), X is selected from the group consisting of H, lower alkyl ($C_1$ to $C_4$), or COOZ, Z represents H, R or a salt forming ion from the group alkali metal, ammonium, or trialkanolammonium, and R is an alkyl group (branched or straight chain) having up to about $C_{20}$ in the chain.

Especially preferred compounds within the above general formula are as follows:

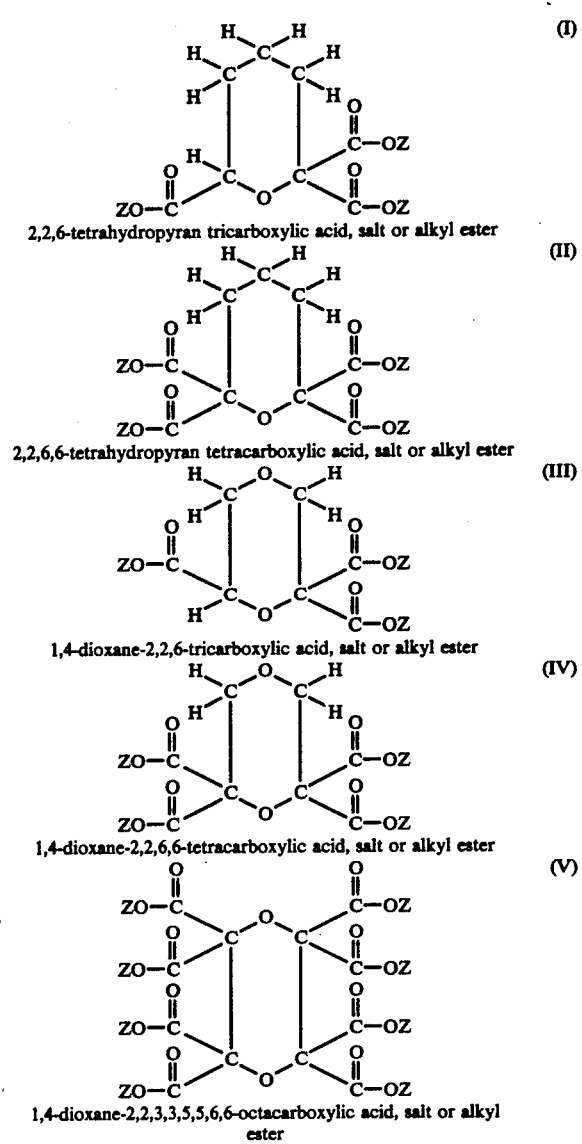

One method for making certain preferred compounds of the invention comprises the basic carboxylation of the 2,6-tetrahydropyran diethyl ester of the formula:

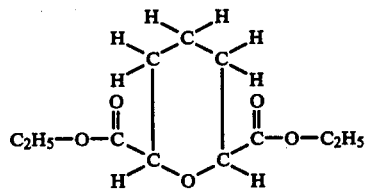

The 2,6-tetrahydropyran diethyl ester is reacted under anhydrous conditions with a strong base such as, sodium phenate, in the presence of carbon dioxide according to the following reaction to produce mixtures of the more highly substituted tetrahydropyran polycarboxylic ester compounds:

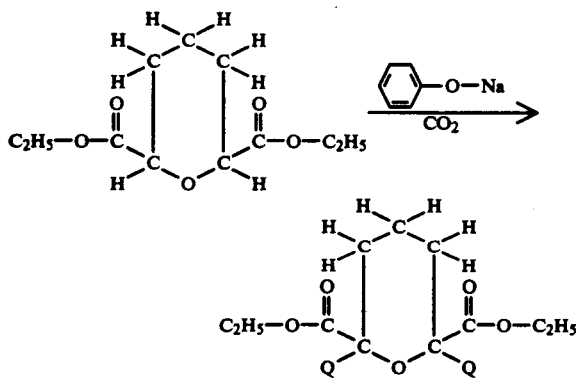

wherein one or both Q's is —CO₂Na and one Q may be H.

The specific component carboxylation products in the mixture may if desired be esterified and separated by distillation or other conventional separatory procedures.

The compositions of the invention comprise various standard solid or liquid detergent compositions containing an amount of the above-described compounds sufficient to enhance the cleaning capacity of the detergent by providing a building, threshold or other function.

Methods for using the compounds of the invention comprise:

(1) formulating detergent compositions by inclusion of from 1 to 90% of the weight of the detergent formulation as compounds of the invention;

(2) softening water by contacting hard water with the compounds of the invention in an amount and for a time sufficient to remove, usually by chelating or sequestering, certain metal ions present in the water, or to complex $Ca^{++}$ and $Mg^{++}$ ions so that they are not available to interfere with the cleaning capacity of soaps or detergents added to the water, and (3) washing soiled articles by contacting the articles with soap or detergent compositions containing or used in the presence of one or more of the compounds of the invention, the compounds being used in amounts sufficient to build or otherwise enhance the cleaning action of the soap or detergent composition.

DETAILED DESCRIPTION OF THE INVENTION

A. Compounds

The compounds of the invention have the molecular structure represented by the following general formula:

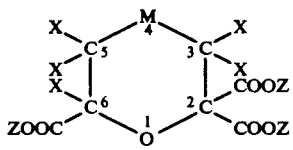

wherein M is O or $CH_2$, X is selected from the group consisting of H or COOZ, Z represents H, R or a salt forming ion from the group alkali metal, ammonium, or trialkanolammonium, and R is an alkyl group (branched or straight chain) having up to about $C_4$ in the chain.

B. Process for Producing the Compounds

It has been found that a suitable method for preparing the compounds of the invention comprises the basic carboxylation of lower tetrahydropyran or 1,4-dioxane polycarboxylic alkyl esters.

The detailed procedure for preparing the compounds of the invention will be better understood by reference to the following examples.

EXAMPLE 1

Preparation of starting material cis-diethyl-2,6-tetrahydropyran dicarboxylate:

(a) Preparation of Diethyl oxalacetate

Diethyl oxalacetate was prepared as a precursor to the preparation of cis-2,6-tetrahydropyran dicarboxylate using the procedure described by A. C. Cope and A. Fournier, Jr., J. Amer. Chem. Soc., 79 3896 (1957).

According to this procedure 150 g of diethyl oxalacetate sodium salt was stirred in a 1000 ml flask with 500 cc of 4 M $H_2SO_4$ and 300 ml of ether. The salt slowly dissolved. Upon complete solution, the ether layer was separated and the aqueous layer was extracted three times with 200 ml portions of ether. The combined ether extracts were backwashed 3 times with water and were then dried with $MgSO_4$. The ether was then removed in vacuo to yield about 100 ml of a light brown, oily liquid which was vacuum distilled at bp 83° C., at 1.5 mm Hg yielding 62 to 82 g of clear, virtually colorless liquid. The nmr was in good agreement with that for diethyl oxalacetate. Unless otherwise indicated, nmr refers to analysis by hydrogen nuclear magnetic resonance.

(b) Preparation of Methylene-bis-(Diethyl oxalacetate)

Further following the procedure of Cope and Fournier, as cited above, 140 g of diethyl oxalacetate freshly prepared as in (a) above and carefully distilled at bp 74° C., and 0.6 mm Hg was added to a 500 ml flask and 32 g of 37% formaldehyde (11.85 g/0.394 mol) was added. Then, 95% ethanol was added to the turbid solution until the solution cleared (about 60 ml of the ethanol was required). Next, 0.65 ml of acetic acid and 2.5 ml of piperidine were added with stirring at 0°-10° C. The mixture was allowed to stand at 0°-5° C., with stirring for 8 hours, at which time 0.30 ml of acetic acid and 1.5 ml of piperidine in 10 ml of 95% ethanol were added. The flask was refrigerated at 5° C., for 36 hours and gave a virtually solid mass of crystals.

Filtration and washing with cold (0° C.) methanol and crude drying gave 89 g of white solid. This material was vacuum dried to yield 78 g of white crystals with a m.p. of 80°-81° C. The nmr was consistent with the expected structure containing a small amount of residual $H_2O$.

(c) Preparation of α,α'-diketopimelic acid

The methylene-bis(diethyl oxalacetate) prepared according to procedure (b) above was then refluxed in excess 50% aqueous hydrochloric acid (HCl) to produce α,α'-diketopimelic acid by the following reaction:

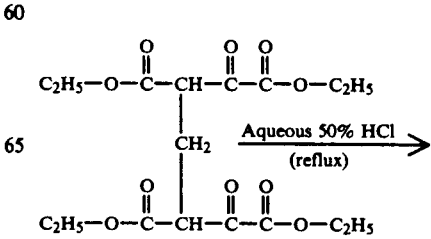

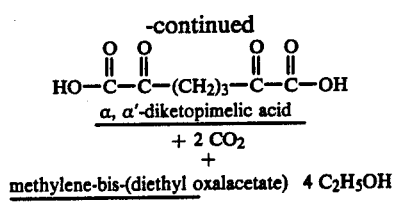

α,α'-diketopimelic acid

+ 2 CO$_2$
+
methylene-bis-(diethyl oxalacetate) 4 C$_2$H$_5$OH

In carrying out this reaction, 140 g of methylene-bis(-diethyl oxalacetate), about 0.36 mol, were heated with 300 ml of 50% (V/V) HCl. The ester slowly melted followed shortly by a noticeable evolution of gas. The mixture was refluxed for 2.5 hours by which time gas evolution had virtually ceased and the solution had darkened considerably.

The aqueous phase was evaporated in vacuo as in the Cope and Fournier procedure, cited above, and the resulting brown solid was treated with 200 ml water and reevaporated to remove residual HCl, then pumped under a vacuum of 0.5 mm Hg for 3 hours to yield 52.0 g of brown solid.

(d) Preparation of 2,6-Pyran Dicarboxylic Acid

The crude product from procedure (c) (α,α'-diketopimelic acid) was dissolved in 250 ml of concentrated sulfuric acid at 15° C. The resulting dark brown solution was stirred for 2.5 hours at 0° C., and then was poured into 2.5 l of ice water with rapid stirring. The crude 2,6-pyran-dicarboxylic acid was isolated by filtration and was washed with copious amounts of water, followed by washings with methanol and ether. The product was then vacuum dried to give 32 g of tan solid.

(e) Preparation of 2,6-Tetrahydropyran Dicarboxylic Acid

The 2,6-pyran dicarboxylic acid prepared in accordance with procedure (d) above, was then hydrogenated to produce 2,6-tetrahydropyran dicarboxylic acid according to the following reaction:

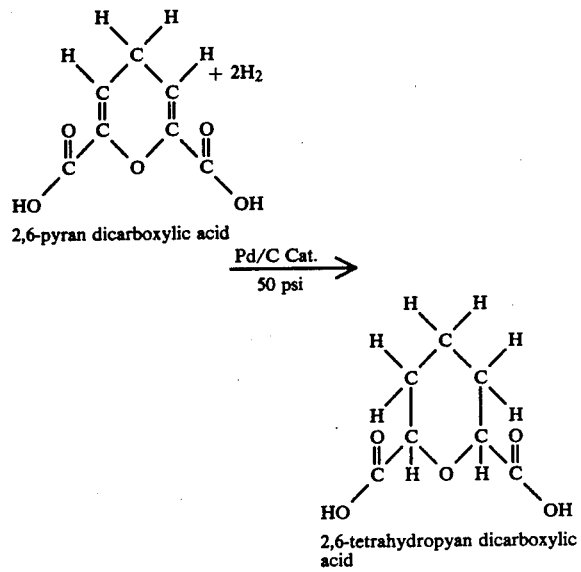

To carry out the foregoing reaction 20.6 g of 2,6-pyran dicarboxylic acid (0.12 mol) was hydrogenated in 250 ml absolute ethanol under between 40-21 lbs H$_2$ using 2.0 g of 10% Pd on carbon as catalyst. Uptake was rapid and appeared complete within 40 minutes. Calculated pressure drop was exactly as observed. After completion of hydrogenation the catalyst was removed by filtration and the ethanol was evaporated off in vacuo leaving about 25 g of a yellow viscous oil.

(f) Preparation of Alkyl Ester of 2,6-Tetrahydropyran dicarboxylic Acid 2,6-tetrahydropyran dicarboxylic acid prepared in accordance with procedure (e) above was esterified by refluxing 11.0 g of the acid in 150 ml of ethanol and 200 ml of benzene overnight with a Dean Stark trap. The azeotrope of benzene, ethanol and H$_2$O was slowly distilled until only 50 ml remained in the reaction flask. This slightly yellow liquid was taken up in 50 ml of additional ether and washed with 100 ml saturated sodium bicarbonate solution, and then with water. The aqueous washings were backwashed with 50 ml ether. The combined organic layers were dried using Na$_2$SO$_4$, filtered and the ether was removed on a rotary evaporator.

Distillation of the residue gave a forerun of bp 93°-95° C., at 0.15 mm then a run of 10.1 g of clear colorless liquid of bp 105°-106° C., at 0.15 mm Hg. This main fraction was shown by nmr to be in excellent agreement with the spectrum predicted for the target diethyl ester of 2,6-tetrahydropyran dicarboxylic acid. The calculated C, H analysis for C$_{11}$H$_{18}$O$_5$ and the C, H analysis found for the product were also in close agreement as shown below:

|  | C % | H % |
|---|---|---|
| Calculated | 57.39 | 7.82 |
| Found | 57.20 | 7.80 |

EXAMPLE 2

Preparation of Disodium 2,6-tetrahydropyran dicarboxylate

To prepare the salt, the oil obtained by procedure (e) above was then taken up in 200 ml of methanol and 21 ml of 50% NaOH were added (a) 10% excess of the amount of NaOH calculated to be required to hydrolyze the 2,6-tetrahydropyran dicarboxylic acid to the corresponding disodium salt. The salt precipitated within several minutes. 200 ml of additional methanol was added and stirring was continued overnight.

Filtration and air drying gave 18.0 g of disodium 2,6-tetrahydropyran dicarboxylate as a white solid. Analysis by nmr was in agreement with the proposed structure.

In addition to serving as a valuable intermediate in the production of the higher carboxylated compounds of the invention, as will be described below, this compound itself, the sodium salt of 2,6-tetrahydropyran dicarboxylic acid, showed substantial utility as a calcium and magnesium ion sequestrant. When tested for sequestration ability by the Divalent Electrode Test Procedure as described by E. A. Matzner et al in an article entitled "Organic Builder Salts as Replacements for Sodium Tripolyphosphate(I)", published in TENSIDE, Vol. 10, 1973, Nos. 3 and 5, pp 119-125 and 239-245, this compound gave values of A=60 mV, B=28 mV, C=6.2 ml and D=9.5 ml for an intensity capacity index of 79% of the index for sodium tripolyphosphate (STP), indicating that the compound has adequate sequestration power to serve as a useful replacement for STP in detergent compositions and washing applications where non-phosphorus compounds or non-phosphorus containing detergent compositions are desired. The high value of A, above, shows that the compound is especially good in binding calcium ion tightly. It is surprisingly better than the analogous five-membered ring, 2,5-tetrahydrofuran dicarboxylate of the prior art, which in comparative tests by the Matzner et al procedure above gave values of A=39 mV, B=21 mV, C=5.5 ml, and D=6.6 ml for an intensity capacity index of 68% of the index for STP. The A value of 60 mV versus 39 mV for these two compounds respectively indicates that the six-membered ring tetrahydropyran analog dicarboxylate of the present invention binds calcium ion significantly and surprisingly more tightly than does the five-membered ring analog, a finding which was unexpected.

Detergency tests in washing cotton and polyester fabric showed an average detergency for the compound equal to from about 75% to 81% of the results obtained using STP formulations.

EXAMPLE 3

Preparation of the tetrahydropyran polycarboxylate compounds of the invention may be accomplished by the basic carboxylation of appropriate starting materials prepared in accordance with the procedures set forth in Example 1, e.g., the dialkyl ester of the 2,6-tetrahydropyran dicarboxylic acid, the preparation of which was described in Example 1, procedure (f).

To carry out this carboxylation a larger sample of the diethyl ester of 2,6-tetrahydropyran dicarboxylic acid was prepared as described in Example 1 and gave 80.5 g of pure material.

A four neck 500 ml flask equipped with a gas dispersion tube, overhead stirrer, reflux condenser and thermometer was charged with 250 ml of either dry hexamethyl phosphorus triamide (HMPA) or dry dimethylformamide (DMF). Then anhydrous sodium phenate, 0.13–0.15 mol, was added. The solution was warmed to 50° C., with stirring while $CO_2$ was bubbled in vigorously for a period of 20 minutes. Then 0.06–0.08 mol of cis-diethyl-2,6-tetrahydropyran dicarboxylate in 50 ml of solvent was added in one portion. The mixture was stirred under a vigorous stream of $CO_2$ for four hours, then cooled and poured into 500 ml of water.

The aqueous solution was then extracted with three portions of either chloroform or methylene chloride. Gas/liquid phase chromotography analysis of the dried extracts indicated only traces of the unreacted cis-diethyl-2,6-tetrahydropyran dicarboxylate.

The aqueous layer was carefully acidified with hydrochloric acid and extracted with four 500 ml portions of ether. The aqueous fraction was saved and the combined ether extracts were concentrated to 200 ml on a rotary evaporator. The ether was then extracted with four 100 ml portions of saturated sodium bicarbonate solution, and the ether was discarded. The bicarbonate solution was then acidified with hydrochloric acid and extracted with four 200 ml portions of ether. The ether was backwashed once with 200 ml of water, once with saturated sodium chloride, and then dried over magnesium sulfate.

The aqueous fraction and ether backwashes were combined with the aqueous fraction from the first extraction and concentrated nearly to dryness. Water was added to just effect solution of the dried residue which was then extracted three times with methylene chloride. These combined extracts were then dried over magnesium sulfate.

The ether and methylene chloride extracts were then concentrated separately yielding a brown viscous oil in each case. Analysis by nmr indicated the presence of phenol, and a mixture of the ethyl ester-acids of the following formulae:

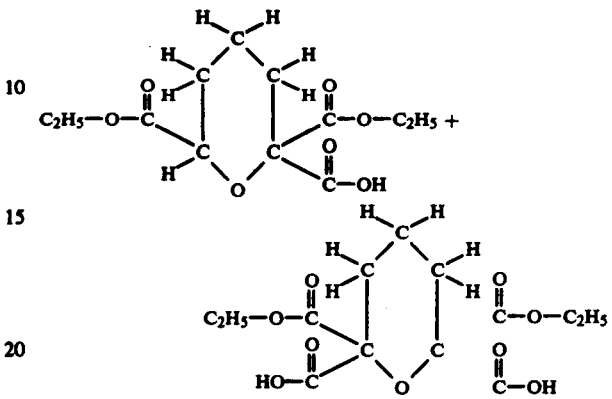

Both of the foregoing mixtures were then treated overnight in methanol (100 ml) with an excess of 50% sodium hydroxide. This precipitated the sodium salts which were isolated by filtration and washed twice with methanol and ether and were vacuum dried overnight. The composition of the dried salts was determined by nmr integrals where possible, and also by derivatization of 20–25 mg with 3 ml of 2.9 M hydrochloric acid in 1-propanol. The mixture of esters was then analyzed by gas/liquid phase chromotography on a 6 ft. column of 3% SE-30 programmed from 150°–250° C., at 10°/min. The results of four runs are set out in Table I:

Table 1

| Phenate Carboxylation of Cis-diethyl-2,6-tetrahydropyran-dicarboxylate | | | | | | |
|---|---|---|---|---|---|---|
| Run No. | Solvent | °C. | Ratio Phenate: III | \multicolumn{3}{l}{Product Ratios} |
| | | | | I: | II: | III |
| 1 | HMPA | 50 | 2 : 1 | 58 | 42 | 0 |
| 2 | DMF | 50 | 2 : 1 | 75 | 15 | 10 |
| 3 | HMPA | 55 | 4 : 1 | 20 | 80 | 0 |
| 4 | DMF | 60 | 8 : 1 | 69 | 31 | 0 |

In the above table the products are as follows:
Product I - Trisodium-2,2,6-tetrahydropyrantricarboxylate
Product II - Tetrasodium-2,2,6,6-tetrahydropyran-tetracarboxylate
Product III - Disodium-2,6-tetrahydropyrandicarboxylate In the above synthesis both HMPA and DMF appear to be the most suitable solvents, the latter being preferred for its easier removal.

EXAMPLE 4

Esters of the trisodium and tetrasodium salts prepared as described above in Example 3 may be prepared in accordance with the following procedure:

A solution of 2.9 M hydrochloric acid in ethanol was prepared by adding 80 ml of acetyl chloride to 320 ml of absolute ethanol at 10°–15° C., under a nitrogen atmosphere. Then 200 ml of this solution were added to a mixture of 21.5 g of the trisodium-2,2,6-tetrahydropyran tricarboxylate and tetrasodium-2,2,6,6-tetrahydropyran tetracarboxylate salts prepared as described above. The esters were separated from the precipitated sodium chloride by washing with ethanol and ether. The organic phase was neutralized with sodium bicarbonate and just enough water to keep the mixture homogeneous. The mixture was then extracted with three 200 ml portions of ether. The combined ether extracts were concentrated on a rotary evaporator to a viscous oil and residual water. The oil was redissolved in 100 ml ether, the water separated, and the ether dried over magnesium sulfate. Gas/liquid phase chromatographic analysis indicated 3% unidentified material, 37% of the triester and 60% of the tetraester. After removal of ether, the residue was distilled through a six inch Vigreaux column. Early and middle fractions contained mixtures of the tri- and tetraesters and the final fractions gave pure tetraester as a viscous colorless liquid with a boiling point of 151°–153° C., at 0.25 mm Hg.

EXAMPLE 5

Referring to Run #4 of Table I which was a phenate carboxylation carried out with 100 g sodium phenate and 25 g of the cis-diethyl-2,6-tetrahydropyran dicarboxylate varying amounts of salts were obtained from certain fractions produced during the synthesis. Specifically, (a) 9.2 g of salts were obtained from the main ether extract, (b) 4.6 g from the methylene chloride extracts of the aqueous fraction, (c) 7.5 g from the concentration of methanol filtrates from the foregoing two steps, and (d) 2.7 g as the result of the addition of ether to Fraction (c). Esterification of Fractions (c) and (d) of Run #4 was carried out as described in Example 4 and yielded after distillation, 5.2 g of trisodium-2,2,6-tetrahydropyran tricarboxylate which was shown by gas/liquid phase chromatography to be greater than 99% pure. The material was a viscous colorless liquid having a boiling point of 122°–123° C., at 0.15 mm Hg.

EXAMPLE 6

The pure trisodium-2,2,6- and tetrasodium-2,2,6,6-tetrahydropyran carboxylate salts can be obtained from the esters.

For example, to obtain the pure trisodium-2,2,6-tetrahydropyran tricarboxylate, 27 g of the corresponding triethyl ester was treated with 11.9 g of sodium hydroxide in 350 ml methanol with stirring overnight. Filtration and washing with methanol and ether gave 19.8 g solid containing both water and methanol of hydration. Redissolving in water and evaporating to dryness, followed by vacuum drying at 80° C., and 0.10 mm Hg gave 15.6 g of trisodium 2,2,6-tetrahydropyran tricarboxylate as a white crystalline powder. Analysis by nmr indicated a 0.75 hydrate. The nmr is in excellent agreement with that expected for the salt. Thermogravimetric analysis of the compound indicates thermal stability up to 325° C. Electrode sequestration data by the method of Example 3 shows the tricarboxylate salt to have $Ca^{++}$ sequestering ability about equivalent to the 2,6-dicarboxylate, but a much superior $Mg^{++}$ sequestering strength. The sequestration index was 115% of that for STP.

Similarly, the pure tetrasodium 2,2,6,6-tetrahydropyran tetracarboxylate was obtained by treating 6 g of the tetraethyl ester with 2.8 g of sodium hydroxide in 200 ml of methanol overnight to give 4.0 g of a yellow solid. An additional sample was obtained on concentration of the filtrate. Both fractions were stirred overnight with an additional 1.0 g of sodium hydroxide in 50 ml methanol. Filtration and washing gave 5.1 g of pale yellow salt shown by derivatization to be 94% tetrasodium-2,2,6,6-tetrahydropyran tetracarboxylate and 6% of the trisodium-2,2,6-tetrahydropyran tricarboxylate. Both fractions were combined and dissolved in 30 ml of water. A trace of insoluble solid was filtered off and the tetrasodium salt was precipitated by the addition of acetone. Filtering and drying at 80° C., and 0.10 mm Hg left 4.2 g of white fluffy solid with no observable colored impurities. Nmr indicated a 0.5 hydrate and is in good accordance with the expected structure. Thermogravimetric analysis indicates a loss of 2.5 percent by weight between 50° and 200° C., and a thermal stability up to 325° C. Electrode sequestration data by the method of Example 3 shows the tetracarboxylate to have $Ca^{++}$ sequestering ability about equivalent to the 2,6-dicarboxylate, but a $Mg^{++}$ sequestering strength greater than either the di- or tricarboxylate. The sequestration index was 123% of that for STP.

EXAMPLE 7

In a manner identical to that described in Example 3, diethyl 1,4-dioxane-2,6-dicarboxylate (by esterification of the acid which is prepared by the procedure described by R. K. Summerbell and J. R. Stephens, J. Am. Chem. Soc., 76, 731 (1954)) is carboxylated with sodium phenate and $CO_2$ in DMF at 50°.

The carboxylated products are isolated by extraction as described in Example 3, and are converted to their sodium salts by sodium hydroxide in methanol and isolated by filtration.

EXAMPLE 8

Pure samples of triethyl 1,4-dioxane-2,2,6-tricarboxylate and tetraethyl 1,4-dioxane-2,2,6,6-tetracarboxylate are obtained by treating the mixture of sodium salts obtained in Example 7 with 2.9 M hydrochloric acid in ethanol, and working up the reaction mixture as described in Example 4. The mixture of esters is then separated into the pure esters by distillation in vacuo through an efficient column.

EXAMPLE 9

The pure trisodium 1,4-dioxane-2,2,6-tricarboxylate and tetrasodium 1,4-dioxane-2,2,6,6-tetracarboxylate salts are obtained by treating the pure esters obtained in Example 8 with sodium hydroxide in methanol. The procedure is that described in Example 6. The salts are isolated by filtration washed with methanol and ether, dried in vacuo at 80° and analyzed by nmr and thermal gravimetric analysis.

EXAMPLE 10

Higher carboxylated products of the 1,4-dioxane system are prepared by phenate carboxylation of tetraethyl 1,4-dioxane-2,3,5,6-tetracarboxylate. This ester is prepared from the corresponding carboxylic acid which is prepared from 2,3,5,6-tetravinyl 1,4-dioxane prepared according to U.S. Pat. No. 3,133,087.

After work-up and isolation the mixture of carboxylated products is converted to a mixture of the sodium salts by treating with sodium hydroxide in methanol, as described in Examples 3 and 7, and isolated by filtration.

EXAMPLE 11

Pure octaethyl 1,4-dioxane-2,2,3,3,5,5,6,6-octacarboxylate is obtained by esterifying the mixture of sodium salts obtained in Example 10 with 2.9 M hydrochloric acid in ethanol as described in Example 4. The pure ester is isolated from the mixture of esters produced, by distillation or chromatography.

EXAMPLE 12

Pure octasodium 1,4-dioxane-2,2,3,3,5,5,6,6-octacarboxylate is obtained by treating the pure octaethyl ester obtained in Example 11 with a 20% excess of sodium hyroxide in water at 60° until the mixture is homogeneous, usually 12-24 hours. The aqueous solution is then added slowly to methanol and the octasodium salt precipitates. The salt is washed with methanol and ether and dried in vacuo at 80° and 1-2 mmHg for several hours.

C. Solid and Liquid Detergent Compositions Comprising the Compounds

The detergent formulations will contain at least 1% by weight and preferably at least 5% by weight of the salt forms of compounds of this invention. In order to obtain the maximum advantages of the builder compositions of this invention the use of from 5% to 80% of these salts is particularly preferred. The salt compounds of this invention can be the sole detergency builder or these compounds can be utilized in combination with other detergency builders which may constitute from 0 to 95% by weight of the total builders in the formulation. By way of example, builders which can be employed in combination with the novel salt compounds of this invention include: water soluble inorganic builder salts, such as alkali metal polyphosphates, i.e., the tripolyphosphates and pyrophosphates, alkali metal carbonates, borates, bicarbonates and silicates, water soluble organic builders, including amino polycarboxylic acids and salts such as alkali metal nitrilotriacetates, cycloalkane polycarboxylic acids and salts, ether polycarboxylates, alkyl polycarboxylates, epoxy polycarboxylates, tetrahydrofuran polycarboxylates such as 2,3,4,5, or 2,2,5,5-tetrahydrofuran tetracarboxylates, benzene polycarboxylates, oxidized starches, amino (trimethylene phosphonic acid) and its salts, diphosphonic acids and salts (e.g., methylene diphosphonic acid; 1-hydroxy ethylidene diphosphonic acid) and the like, and water insoluble builders, such as, aluminosilicates, zeolites and the like.

The detergent formulations will generally contain from 5% to 95% by weight total builder (although greater or less quantities may be employed if desired) which, as indicated above, may be solely the builder salt compounds of this invention or mixtures of such compounds with other builders. The total amount of builder employed will be dependent on the intended use of the detergent formulation, other ingredients of the formulation, pH conditions and the like. For example, general laundry powder formulations will usually contain 20% to 60% builder; liquid dishwashing formulations 11% to 12% builder; machine dishwashing formulations 60% to 90% builder. Optimum levels of builder content as well as optimum mixtures of builders of this invention with other builders for various uses can be determined by routine tests in accordance with conventional detergent formulation practice.

The detergent formulations will generally contain a water soluble detergent surfactant although the surfactant ingredient may be omitted from machine dishwashing formulations. Any water soluble anionic, nonionic, zwitterionic or amphoteric surfactant can be employed.

Examples of suitable anionic surfactants include soaps such as the salts of fatty acids containing about 9 to 20 carbon atoms, e.g., salts of fatty acids derived from coconut oil and tallow; alkyl benzene sulfonates—particularly linear alkyl benzene sulfonates in which the alkyl group contains from 10 to 16 carbon atoms; alcohol sulfates; ethoxylated alcohol sulfates; hydroxy alkyl sulfonates; alkenyl and alkyl sulfates and sulfonates; monoglyceride sulfates; acid condensates of fatty acid chlorides with hydroxy alkyl sulfonates and the like.

Examples of suitable nonionic surfactants include alkylene oxide (e.g. ethylene oxide) condensates or mono and polyhydroxy alcohols, alkyl phenols, fatty acid amines, and fatty amines; amine oxides, sugar derivatives such as sucrose monopalmitate; long chain tertiary phosphine oxides, dialkyl sulfoxides; fatty acid amines, (e.g., mono or diethanol amides of fatty acids containing 10 to 18 carbon atoms), and the like.

Examples of suitable zwitterionic surfactants include derivatives of aliphatic quaternary ammonium compounds such as 3-(N,N-dimethyl-N-hexadecyl ammonio)propane-1-sulfonate and 3-(N,N-dimethyl-N-hexadecyl ammonio)-2-hydroxy propane-1-sulfonate.

Examples of suitable amphoteric surfactants include betains, sulfobetains and fatty acid imidazole carboxylates and sulfonates.

It will be understood that the above examples of surfactants are by no means comprehensive and that numerous other surfactants are known to those skilled in the art. It will be further understood that the choice and use of surfactants will be in accordance with well understood practices of detergent formulation. For example, anionic surfactants, particularly linear alkyl benzene sulfonate are preferred for use in general laundry formulations, whereas low foaming nonionic surfactants are preferred for use in machine dishwashing formulations.

The quantity of surfactant employed in the detergent formulations will depend on the surfactant chosen and the end use of the formulation. In general, the formulations will contain from 5% to 50% surfactant by weight, although as much as 95% or more surfactant may be employed if desired. For example, general laundry powder formulations normally contain 5% to 50%, preferably 15% to 25% surfactant; machine dishwashing formulations 0.5% to 5%; liquid formulations 20% to 45%. The weight ratio of surfactant to builder will generally be in the range of from 1:12 to 2:1.

In addition to builder and surfactant components, detergent formulations may contain fillers such as sodium sulfate and minor amounts of bleaches, dyes, optical brighteners, soil anti-redeposition agents, perfumes and the like.

In machine dishwashing compositions the surfactant will be a low-foaming anionic or preferably, nonionic surfactant which will constitute 0 to 5% of the formulation.

The term "low-foaming" surfactant connotes a surfactant which, in the foaming test described below, reduces the revolutions of the washer jet-spray arm during the wash and rinse cycles less than 15%, preferably less than 10%.

In the foaming test, 1.5 g of surfactant is added to a 1969 Kitchen-Aid Home Dishwasher, Model No. KOS-16, manufactured by Hobart Manufacturing Company which is provided with means for counting revolutions of the washer jet-spray arm during wash and rinse cycles. The machine is operated using distilled water feed at a machine entrance temperature of 40° C. The number of revolutions of the jet-spray arm during the wash and rinse cycles is counted. The results are compared with those obtained by operation of the machine using no surfactant charge and the percentage decrease in the number of revolutions is determined.

The surfactant should, of course, be compatible with the chlorine containing component hereinafter discussed. Examples of suitable nonionic surfactants include ethoxylated alkyl phenols, ethoxylates alcohols (both mono- and dihydroxy alcohols), polyoxyalkylene glycols, aliphatic polyethers and the like. The widely commercially utilized condensates of polyoxypropylene glycols having molecular weight of from about 1400 to 2200 with ethylene oxide (the ethylene oxide constituting 5 to 35 weight percent of the condensate) are, for example, advantageously used in the machine dishwashing formulations of this invention.

Suitable low-foaming anionic surfactants include alkyl diphenyl ether sulfonates such as sodium dodecyl diphenyl ether disulfonates and alkyl naphthalene sulfonates.

Mixtures of suitable low-foaming surfactants can be utilized if desired.

In addition, machine dishwashing formulations will contain sufficient chlorine providing compound to provide 0.5% to 2% available chlorine. For example, the formulation may contain from 0.5% to 5%, preferably 1% to 3% of a chlorocyanurate or from 10% to 30% chlorinated trisodium phosphate. Suitable chlorocyanurates are sodium and potassium dichlorocyanurate; [(monotrichloro)tetra(monopotassium dichloro)]pentaisocyanurate; (monotrichloro) (monopotassium dichloro) diisocyanurate.

Machine dishwashing compositions should additionally contain from 5% to 30% soluble sodium silicate having an $SiO_2$ to $Na_2O$ mole ratio of from 1:1 to 3.2:1 preferably about 2.4:1 to inhibit corrosion of metal parts of dishwashing machines and provide over-glaze protection to fine china.

Machine dishwashing compositions will generally contain at least 10%, preferably at least 20% builder, up to a maximum of about 90% builder. The new salt compounds of this invention should constitute at least 5% of the weight of the machine dishwashing formulation.

D. Washing Processes Employing the Compounds

The compounds of this invention may be employed in water softening and washing processes in accordance with well known techniques. In either case the process generally involves contacting the water to be softened or the water to be used in the washing process with an effective amount of the compounds of the invention or compositions containing the compounds of the invention. The result in either case is the chelation or sequestration of certain metal ions present in the water so that the aqueous system can perform better as a cleaning or washing material.

What is claimed is:

1. A detergent formulation comprising:
   (a) from 0.5 to 95% by weight of a surfactant selected from the group consisting of water soluble anionic, nonionic, amphoteric and zwitterionic surfactants, and
   (b) from 1 to 95% by weight of a compound of the molecular structure represented by the formula:

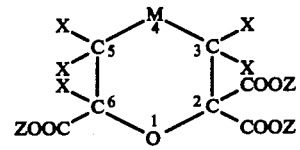

wherein M is O or $CY_2$, where Y is H or lower alkyl ($C_1$ to $C_4$), X is selected from the group consisting of H, lower alkyl ($C_1$ to $C_4$), or COOZ, Z represents H, R or a salt forming ion from the group alkali metal, ammonium, or trialkanolammonium, and R is an alkyl group (branched or straight chain) having up to about $C_{20}$ in the chain.

2. The formulation of claim 1 wherein the compound (a) is present in an amount of from 5 to 95% and component (b) is present in an amount of from 5 to 95%.

3. The composition of claim 1 wherein the compound of (b) is trisodium-2,2,6-tetrahydropyran-tricarboxylate.

4. The composition of claim 1 wherein the compound of (b) is tetrasodium-2,2,6,6-tetrahydropyran tetracarboxylate.

5. A machine dishwashing composition comprising:
   (a) from 0 to 5% by weight of a surfactant selected from the group consisting of low-foaming anionic and nonionic surfactants and mixtures thereof,
   (b) a chlorine providing material in an amount sufficient to provide from about 0.5 to 2% by weight of available chlorine,
   (c) from 5 to 30% by weight soluble sodium silicate having an $SiO_2$ to $Na_2O$ mole ratio of from 1:1 to 3.2:1, and
   (d) from 5 to 90% by weight of one or more compounds having the molecular structure represented by the formula:

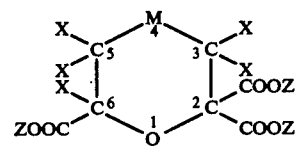

wherein M is O or $CY_2$, where Y is H or lower alkyl ($C_1$ to $C_4$), X is selected from the group consisting of H, lower alkyl ($C_1$ to $C_4$), or COOZ, Z represents H, R or a salt forming ion from the group alkali metal, ammonium, or trialkanolammonium, and R is an alkyl group (branched or straight chain) having up to about $C_{20}$ in the chain.

6. The composition of claim 5 wherein the compound of (d) is trisodium-2,2,6-tetrahydropyran-tricarboxylate.

7. The composition of claim 5 wherein the compound of (d) is tetrasodium-2,2,6,6-tetrahydropyran tetracarboxylate.

8. A method for washing articles comprising:
   contacting said articles with an aqueous detergent composition,
   said aqueous detergent composition comprising, dissolved in the water of said aqueous composition, a compound of the molecular structure represented by the formula:

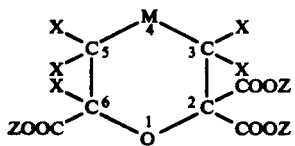

wherein M is O or $CY_2$, where Y is H or lower alkyl ($C_1$ to $C_4$), X is selected from the group consisting of H, lower alkyl ($C_1$ to $C_4$), or COOZ, Z represents H, R or a salt forming ion from the group alkali metal, ammonium, or trialkanolammonium, and R is an alkyl group (branched or straight chain) having up to about $C_{20}$ in the chain.

9. The composition of claim 8 wherein said compound is trisodium-2,2,6-tetrahydropyran-tricarboxylate.

10. The composition of claim 8 wherein said compound is tetrasodium-2,2,6,6-tetrahydropyran tetracarboxylate.

* * * * *